(12) United States Patent  (10) Patent No.: US 7,797,049 B2
Christopherson et al.  (45) Date of Patent: Sep. 14, 2010

(54) NEUROSTIMULATION DELIVERY DURING TRANSURETHRAL PROSTATE TREATMENT

(75) Inventors: Mark A. Christopherson, Shoreview, MN (US); John M. Swoyer, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 51 days.

(21) Appl. No.: 11/966,024

(22) Filed: Dec. 28, 2007

(65) Prior Publication Data

US 2008/0103496 A1 May 1, 2008

Related U.S. Application Data

(62) Division of application No. 10/424,118, filed on Apr. 25, 2003, now Pat. No. 7,340,300.

(51) Int. Cl.
*A61N 1/28* (2006.01)
*A61N 1/34* (2006.01)
(52) U.S. Cl. .......................... 607/39; 607/46
(58) Field of Classification Search .................. 607/39, 607/45
See application file for complete search history.

(56) References Cited

U.S. PATENT DOCUMENTS

| 6,238,393 | B1 * | 5/2001 | Mulier et al. ................. 606/41 |
| 6,551,300 | B1 | 4/2003 | McGaffigan |
| 6,852,091 | B2 | 2/2005 | Edwards et al. |
| 2001/0031941 | A1 * | 10/2001 | Edwards et al. ............... 604/22 |

* cited by examiner

*Primary Examiner*—Michael Kahelin
(74) *Attorney, Agent, or Firm*—Scott A. Marks

(57) ABSTRACT

In general, the invention provides a transurethral ablation device comprising an electrode for delivery of neurostimulation therapy to a patient to prevent or alleviate pain experienced during the course of a transurethral ablation procedure. The device may include a conductive ablation needle that delivers electrical current for ablation of prostate tissue, as well as neurostimulation current to prevent or alleviate pain encountered in response to the ablation current. In this sense, the ablation needle is integrated with a neurostimulation electrode. Alternatively, the device may incorporate a dedicated neurostimulation electrode independently of the ablation needle, either on the needle or on a catheter body that carries the needle.

18 Claims, 8 Drawing Sheets

NEUROSTIMULATION DELIVERY DURING TRANSURETHRAL PROSTATE TREATMENT

This application is a divisional of U.S. patent application Ser. No. 10/424,118, filed Apr. 25, 2003, now allowed. The entire content of this application is incorporated herein by reference.

FIELD OF THE INVENTION

The invention relates generally to prostate treatment and, more particularly, to techniques for transurethral treatment of benign prostatic hypertrophy (BPH).

BACKGROUND

Benign prostatic hypertrophy or hyperplasia (BPH) is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling.

One surgical procedure for treating BPH is transurethral needle ablation (TUNA). The TUNA technique involves transurethral delivery of an electrically conductive needle to the prostate site. The needle penetrates the prostate in a direction generally perpendicular to the urethral wall, and delivers electrical current to ablate prostate tissue. The electrical current heats tissue surrounding the needle tip to destroy prostate cells, and thereby create a lesion within the prostate gland. The destroyed cells may be absorbed by the body, infiltrated with scar tissue or become non-functional.

Other transurethral ablation procedures involve delivery of microwave, radio frequency, acoustic, and light energy to the prostate gland. In addition, some procedures involve delivery of localized chemotherapy, drug infusions, collagen injections, or injections of agents which are then activated by light, heat or chemicals to destroy prostate tissue. These procedures, as well as the TUNA procedure, involve tissue trauma that can be painful for the patient. Accordingly, minimization of patient pain continues to be an objective in the design and delivery of transurethral prostate treatment procedures.

U.S. Pat. No. 6,551,300 to McGaffigan discloses a transurethral ablation device that delivers a topically applied anesthetic agent gel to a urethral wall. U.S. Published Patent Application no. 2002/0183740 to Edwards et al. discloses a transurethral ablation device to ablate prostate tissue via electrically conductive needles. Table 1 below lists documents that disclose devices for transurethral ablation of prostate tissue.

TABLE 1

| Patent Number | Inventors | Title |
| --- | --- | --- |
| 2002/0183740 | Edwards et al. | Medical probe device and method |
| 6,551,300 | McGaffigan | Device and method for delivery of topically applied local anesthetic to wall forming a passage in tissue |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY

The present invention is directed to a device and method for delivery of neurostimulation during transurethral prostate treatment, e.g., transurethral ablation of prostate tissue to alleviate BPH. The invention has certain objects. That is, various embodiments of the present invention provide solutions to one or more problems existing in the prior art with respect to the ablation of prostate tissue.

The problems include, for example, pain associated with some existing transurethral ablation techniques. In existing techniques, such as the TUNA procedure, electrode needles are deployed into the urethral wall to penetrate prostate tissue to be ablated. The needles deliver energy to ablate prostate tissue and thereby form lesions. Penetration of the needles and delivery of ablation energy can be painful for the patient. Delivery of general anesthetic significantly complicates the surgical procedure, takes time for administration, affects the patient's overall system and well being. Delivery of local anesthetics can provide a more localized effect, but requires time for administration and patient uptake for effective pain prevention or relief. In addition, the effects of general or localized anesthetic agents can linger following completion of the procedure.

Various embodiments of the present invention have the object of solving at least one of the foregoing problems. For example, it is an object of the present invention to overcome at least some of the disadvantages of the foregoing procedures by providing a transurethral ablation procedure that achieves localized pain prevention or relief during the course of the procedure. As another object, the invention provides an alternative mode of pain prevention or relief that does not require delivery of general or local anesthetic agents. It is another object to provide a mode of pain prevention and relief that offers virtually immediate effects and can be terminated abruptly to avoid lingering effects Various embodiments of the invention may possess one or more features capable of fulfilling the above objects. In general, the invention provides a transurethral ablation device comprising an electrode for delivery of neurostimulation therapy to a patient to prevent or alleviate pain experienced during the course of a transurethral ablation procedure. The device may include a conductive ablation needle that delivers electrical current for ablation of prostate tissue, as well as neurostimulation current to prevent or alleviate pain encountered in response to the ablation current. In this sense, the ablation needle is integrated with a neurostimulation electrode. Alternatively, the device may incorporate a dedicated neurostimulation electrode independently of the ablation needle, either on the needle or on a catheter body that carries the needle. As a further alternative, a neurostimulation electrode may be provided with other types of ablation probes, such as laser, microwave, or cryogenic probes.

The invention also provides a transurethral ablation procedure embodied by a method for use of the ablation device described above. The method involves, for example, inserting a distal end of a catheter into a urethra of a male patient, deploying an ablation probe, activating neurostimulation therapy, and then applying ablation energy. In this manner, neurostimulation therapy can be activated to reduced pain associated with application of the ablation energy. In some embodiments, neurostimulation therapy may be applied before the ablation probe is deployed so that pain associated with penetration of the urethral wall can also be reduced. Also, neurostimulation therapy can be applied to the urethral wall during deployment and withdrawal of the catheter to reduce patient pain and discomfort.

In comparison to known implementations of transurethral prostate ablation, various embodiments of the present invention may provide one or more advantages. In general, the invention may reduce the pain associated with some existing transurethral ablation technique. In addition, the invention offers a localized treatment for alleviation of pain that does not require delivery of anesthetic, and does not suffer from delays in administration and uptake of such anesthetics. Instead, neurostimulation can be started and stopped substantially instantaneously, permitting immediate application of pain prevention or relief when needed, and avoiding the lingering effects of anesthetic agents. In addition, in some embodiments, neurostimulation can be delivered by the same device used to perform the transurethral ablation procedure, making the procedure less complex, quicker, and more convenient for the surgeon.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
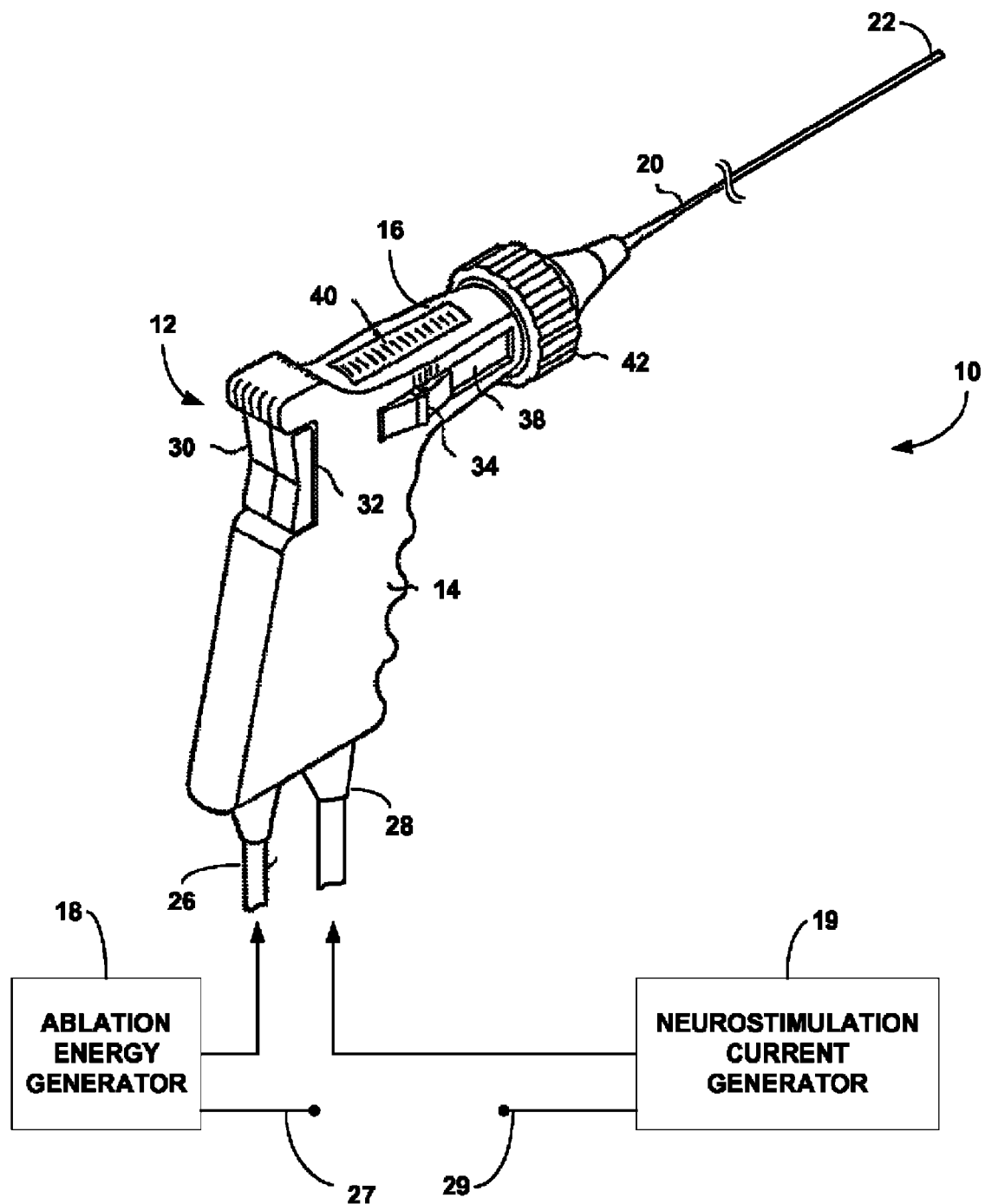
FIG. 1 is a schematic diagram illustrating a device for transurethral ablation of prostate tissue in accordance with the invention.

FIG. 1 is a schematic diagram illustrating a device 10 for transurethral ablation of prostate tissue. In accordance with the invention, device 10 is capable of delivering neurostimulation to a patient to prevent or relieve pain associated with the transurethral ablation procedure. As shown in FIG. 1, device 10 includes a manipulator 12 having a handle 14, a barrel 16, an ablation energy generator 18, a neurostimulation current generator 19, and a transurethral ablation catheter 20 extending from the barrel. Catheter 20 is sized for insertion into a urethra of a male patient. As will be described, distal end 22 of catheter 20 includes an ablation probe to deliver ablation energy to a target tissue site with the prostate, and a neurostimulation therapy electrode to deliver neurostimulation current to the an area proximate the target tissue site.

Ablation energy generator 18 delivers electrical current, e.g., radio frequency (RF) electrical current, to manipulator 12 via an electrical connector 26. Manipulator 12 includes internal electrical conductors to transmit the electrical current to catheter 20. Similarly, catheter 20 includes one or more electrical conductors to transmit the electrical current to distal end 22 for use in generating ablation energy. Ablation energy generator 18 is also coupled to a reference electrode 27, which may be placed on or within the patient's body to complete an electrical circuit for transmission of current to the target tissue site.

Alternatively, ablation energy generator 18 may deliver other forms of ablation energy such as laser energy or microwave energy. As a further alternative, ablation energy generator 18 may supply a cryogenic substance to the ablation probe to cryogenically kill cells within the target tissue site. In these cases, device 10 includes appropriate media, such as electrical conductors, optical waveguides, cryogenic tubing, or the like, to transmit the ablation energy to the distal end 22 of catheter 20.

As further shown in FIG. 1, device 10 includes a neurostimulation current generator 19, which transmits neurostimulation current to a neurostimulation electrode at the distal tip 22 of catheter 20 via an electrical connector 28. Again, manipulator 12 includes internal electrical conductors to transmit the neurostimulation current to catheter 20, and conductors within the catheter to transmit the neurostimulation current to distal tip 22. Neurostimulation current generator is also coupled to a reference electrode 29, which may be placed on or within the patient's body, to complete an electrical circuit for delivery of neurostimulation current to a location proximate the target tissue site.

In some embodiments, neurostimulation current generated by neurostimulation current generator 19 may travel along common conductors with ablation current generated by ablation energy generator 18. In particular, common electrical conductors within manipulator 12, catheter 20, or both may carry both neurostimulation current and ablation current. In this case, the neurostimulation current may be transmitted in a time multiplexed, i.e., time-interleaved, manner with the ablation current. Alternatively, the neurostimulation current may be superimposed on the ablation current, which typically occupies a much higher frequency range. In these cases, neurostimulation current can be delivered at the same time ablation energy is delivered. In other embodiments, neurostimulation current and ablation current are transmitted along separate electrical conductors or at distinct times prior to or during the course of the ablation procedure.

In the example of FIG. 1, manipulator 12 includes rocker switches 30, 32. Switch 30 permits a surgeon to control the application of electrical ablation current (or other ablation energy) supplied by current generator 18 to the target tissue site. Switch 32 permits the surgeon to control the application of neurostimulation current supplied by neurostimulation current generator to the target tissue site. A slider bar 34, disposed in channel 38, permits the surgeon to move an ablation probe longitudinally within catheter 20. An indicator 40 tracks the movement of the ablation probe for overhead visibility by the surgeon. Wheel 42 permits rotation of catheter 20, e.g., to place the ablation probe at desired radial positions within the urethra. Notably, device 10 may include one or more ablation probes, such as multiple ablation needles. Accordingly, multiple needles may be actuated simultaneously or independently using manipulator 12.

Figure 2:
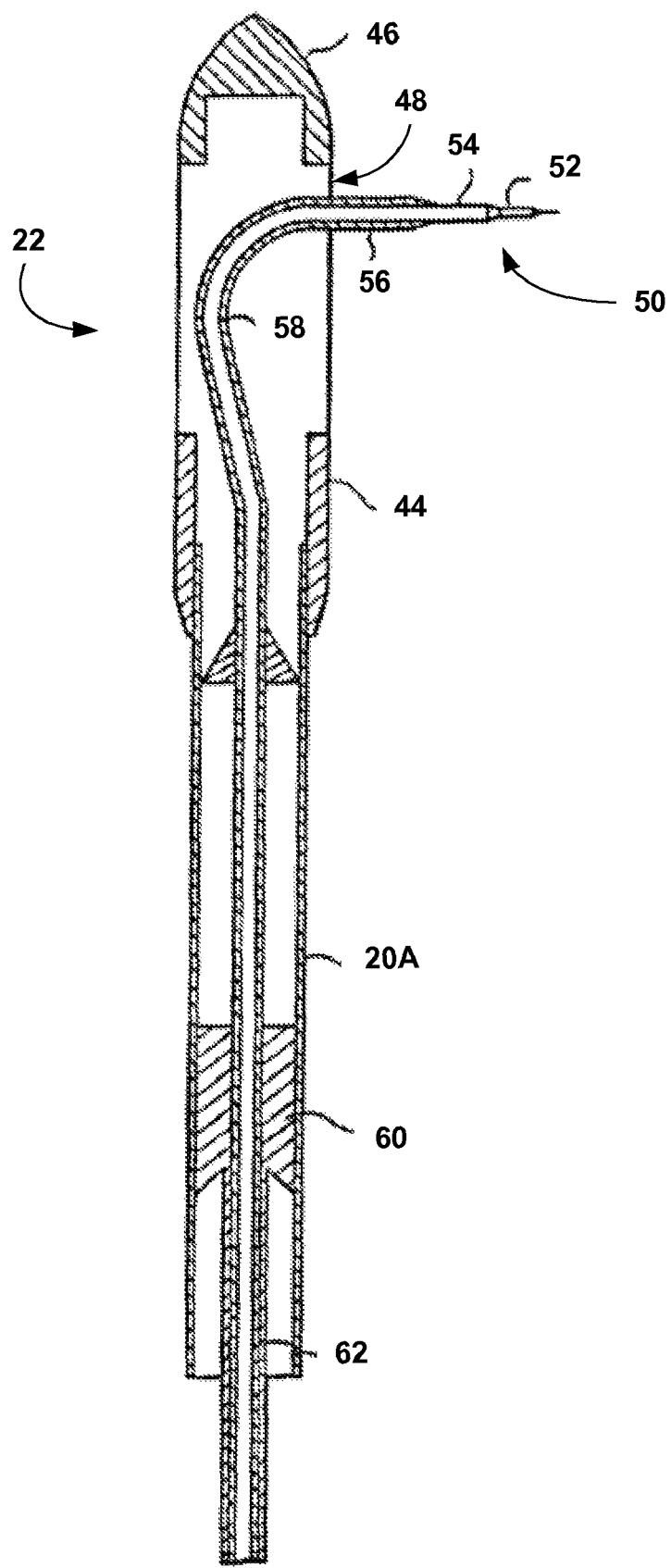
FIG. 2 is an enlarged cross-sectional side view of the distal end of the device of FIG. 1.

FIG. 2 is an enlarged cross-sectional side view of the distal end 22 of a catheter 20A suitable for use with device 10 of FIG. 1. As shown in FIG. 2, catheter 20 is connected to a probe guide housing 44 with a nose 46. Probe guide housing 44 defines a side port 48 that permits a probe 50 to extend outward from catheter 20A. Needle 52 may comprise a solid core needle coaxially positioned within a conductive tube 54, both of which are preferably constructed of a highly flexible, conductive metal such as nickel-titanium alloy, tempered steel, stainless steel, beryllium-copper alloy and the like. Nickel-titanium and similar highly flexible, shaped memory alloys are preferred.

Needle 52 may be axially or longitudinally moveable within tube 54. Tube 54 is enclosed within an non-conductive, dielectric sleeve 56 which is longitudinally moveable along the tube. Probe guide housing 44 has a guide channel 58 which is curved to permit longitudinal advancement of the flexible probe 50. Sleeve 56 is connected to an annular cylinder 60 connected with a longitudinal thrust tube 62. Longitudinal movement of thrust tube 62 causes a corresponding longitudinal movement of sleeve 56 along tube 54. The sleeve movement can be used to vary and control the length of tube 54 and needle 52 exposed to surrounding tissue and control the amount of energy delivered to the target tissue.

In operation, ablation energy generator 18 delivers electrical current to needle 52 via conductive tube 54. In the example of FIG. 2, conductive tube 54 is also used to deliver neurostimulation current to the patient. To commence the ablation procedure, probe 50 is extended from probe guide housing 44 and delivered into prostatic tissue underneath or behind the prostatic urethra. The surgeon activates neurostimulation current generator 19 to deliver neurostimulation current to the tissue via needle 52. Then, the surgeon activates ablation energy generator 18 to deliver ablation current to the tissue site via needle 52. The ablation current ablates a portion of the prostate tissue.

During ablation, the neurostimulation current may continue to be applied via needle 52. In this manner, the neurostimulation current relieves, and possibly prevents, the sensation of pain by the patient during the ablation procedure. Again, the neurostimulation current may be superimposed on, or time-multiplexed with, the ablation current. Alternatively, the neurostimulation current may be delivered just prior to delivery of the ablation current and just after delivery of the ablation current. Preferably, however, the neurostimulation current is applied before, during and after delivery of the ablation current.

For example, the neurostimulation current may be applied for a few seconds in advance of the ablation current, then during delivery of the ablation current, and then for a few seconds or even minutes following termination of the ablation current. In this manner, the neurostimulation current prepares the tissue site for ablation, supplies pain suppression during the procedure, and extends pain suppression for a limited period of time after the procedure.

In general, the electrical ablation current may be selected to provide pulsed or sinusoidal waveforms, cutting waves, or blended waveforms that are effective in killing cells within the tissue site. In addition, the electrical current may include ablation current followed by current sufficient to cauterize blood vessels. The electrical current may be accompanied by delivery of electrolytes to yield desired conduction characteristics. In addition, the ablation current and the neurostimulation current may be accompanied by delivery of pain relief substances, including anesthetic agents such as Lidocaine to reduce pain experienced by the patient during the course of the procedure. Pain relief substances may provide an added measure of pain relief. In terms of time, simplicity and convenience, however, delivery of neurostimulation therapy without anesthetic agents is desirable.

The characteristics of the electrical ablation current are selected to achieve significant cell destruction within the target tissue site. The electrical ablation current may radio frequency current in the range of approximately 5 to 300 watts, and more preferably 5 to 50 watts, and can be applied for a duration of approximately 15 seconds to 3 minutes. Electrical ablation current flows between ablation needle 52 and a reference electrode placed within or on the surface of the patient's body. Alternatively, ablation needle 52 may take the form of a bipolar probe that carries two or more ablation electrodes, in which case the current flows between the electrodes.

The characteristics of the neurostimulation current are selected to achieve a significant degree of pain relief for the patient in the localized region surrounding the target tissue site. In particular, the neurostimulation current is selected to provide electrical stimulation waveforms known to be effective in blocking pain signals in the nervous system. As an illustration, the frequency of the neurostimulation current may fall in the range of approximately 50 to 150 Hz. Each pulse may have an amplitude in the range of approximately 1 to 10 volts, and more preferably approximately 1 to 5 volts. The waveform of the neurostimulation current may be, for example, pulsed or sinusoidal. If the neurostimulation current is pulsed, the pulse width may be in the range of approximately 100 to 400 microseconds.

With delivery of neurostimulation current, device 10 enables the transurethral ablation procedure to be completed in a reduced number of steps. For example, delivery of general or local anesthetic agents, although optional, is unnecessary. As a result, there is no delay in the procedure for administration of the anesthetic agent and uptake by the patient. For example, there is no need to wait for the patient to achieve a state of anesthesia. Instead, the neurostimulation current can be applied instantaneously with rapid effect. Moreover, the neurostimulation current can be terminated instantaneously. In this case, the effects of the neurostimulation current subside rapidly, in contrast to the lingering effects of anesthetic agents, which can impair or incapacitate the patient for a period of time following the procedure.

Figure 3:
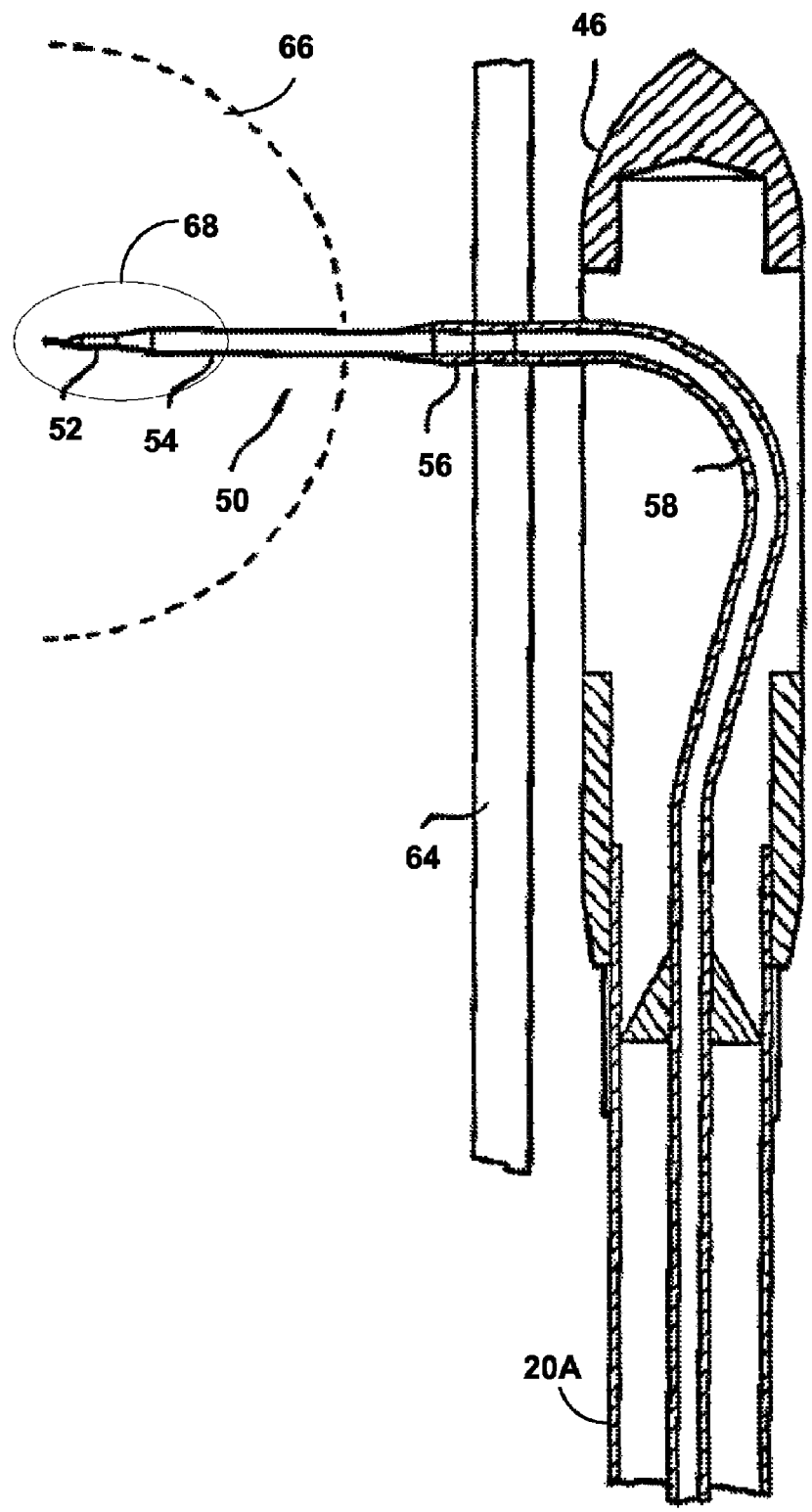
FIG. 3 is an enlarged cross-sectional side view of the distal end of the device of FIG. 1 with an ablation probe extended into a tissue site.

FIG. 3 is an enlarged side view of distal end 22 of catheter 20A of device 10 of FIG. 2. Using manipulator 12 and wheel 42 (FIG. 1), the surgeon may initially translate and rotate catheter 20A, for example, to bring probe 50 into alignment with one of the lateral prostate lobes. As will be described, following ablation of tissue within the desired lobe, the surgeon may rotate catheter 20A to access the other lateral lobe and the medial lobe, if desired. Alternatively, catheter 20A may include two or more probes oriented to penetrate the lateral lobes simultaneously. Longitudinal and radial positioning of catheter 20A may be aided by imaging techniques such as ultrasound, MRI or the like. In addition, in some embodiments, catheter 20A may incorporate an endoscopic imaging device to permit direct acquisition of images from within the urethra.

As shown in FIG. 2, upon deployment of distal end 22 proximate a target tissue site within the urethra, ablation probe 50 is inserted into the captured tissue. For example, a surgeon may actuate slider bar 34 in manipulator 12 (FIG. 1) to drive probe 50 through urethral wall 64 and into prostate tissue 66. When probe 52 is lodged in tissue 66, the surgeon activates neurostimulation current generator 19 to deliver neurostimulation therapy to the tissue site via needle 52. Upon application of ablation current, needle 52 ablates a zone 68 of tissue surrounding probe 50.

In the example of FIG. 3, ablation probe 50 is an electrically conductive needle that applies electrical current to the tissue. In particular, electrical current flows between needle 52 and a reference electrode coupled to ablation energy generator 18 and placed on or within the patient. Alternatively, ablation probe 50 may be configured as a bipolar instrument that carries two or more electrodes for localized current flow. In either case, delivery of both ablation current and neurostimulation current via needle 52 alleviates or reduces pain associated with the ablation procedure.

Figure 4:
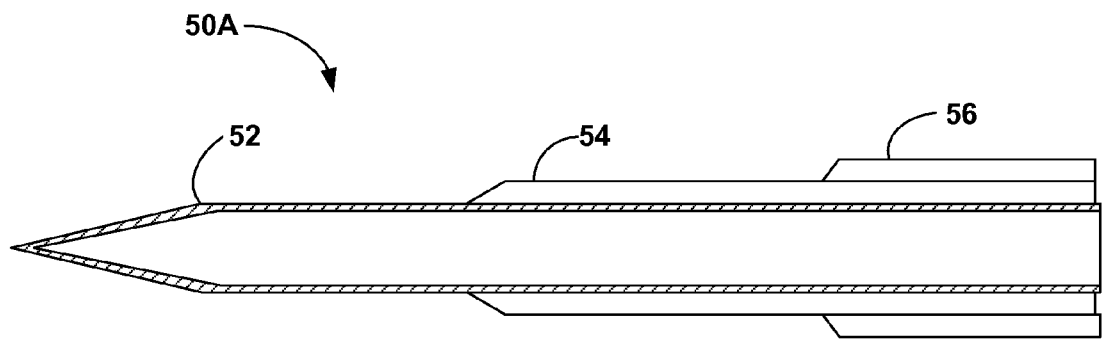
FIG. 4 is an enlarged cross-sectional side view of an ablation probe with an integrated neurostimulation electrode for the device of FIG. 1.
Figure 5:
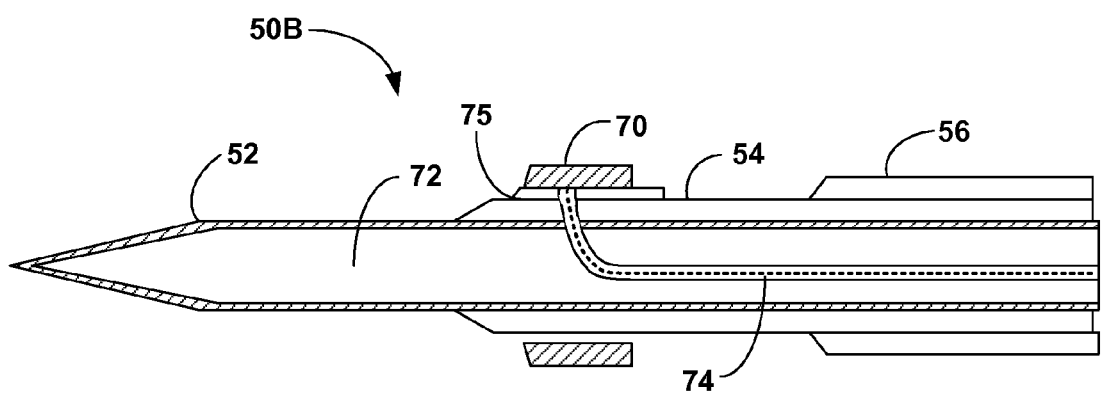
FIG. 5 is an enlarged cross-sectional side view of an ablation probe with a discrete neurostimulation electrode for the device of FIG. 1.

FIG. 4 is an enlarged cross-sectional side view of an ablation probe 50A with an integrated neurostimulation electrode for device 10 of FIG. 1. As shown in FIG. 4, ablation probe 50 includes conductive needle 52, tube 54, and insulative sleeve 56. Accordingly, ablation probe 50A conforms substantially to the ablation probe depicted in FIGS. 2 and 3. Therefore, in the example of FIG. 4, both ablation current and neurostimulation current are transmitted via the same needle 52. To that end, manipulator 12 includes an internal switch that serves to connect ablation energy generator 18 and neurostimulation current generator 19 to a common conductor connected to tube 54 or a conductor within catheter 20 that leads to tube 54. FIG. 5 is an enlarged cross-sectional side view of an ablation probe 50B with a discrete neurostimulation electrode 70 for device 10 of FIG. 1.

In contrast to ablation probe 50A, ablation probe 50B has a separate electrode 70 and conductive path for delivery of neurostimulation current. In particular, as shown in FIG. 5, needle may be constructed as a hollow needle with an inner lumen 72 that accommodates an insulated conductor 74. Conductor 74 travels the length of probe 50 and catheter 20, and extends through tube 54 and an insulating layer 75 to contact electrode 70. Electrode 70 may take the form of a conductive pad. Alternatively, electrode 70 may be a ring electrode that extends about tube 54 and insulating layer 75. Electrode 70 represents a monopolar arrangement in which the electric potential carried by the electrode is referenced to catheter 20 or an external ground pad. In some embodiments, however, two or more electrodes can be provided on ablation probe 50B to form one or more possible bipolar arrangements for targeted, localized delivery of neurostimulation therapy.

Upon penetration of the target tissue site by probe 50, neurostimulation current is delivered via discrete electrode 70. Then, ablation current is delivered via needle 52 to ablate prostate tissue within the target tissue site. The neurostimulation current and ablation current, although delivered via separate electrodes, may be delivered at the same time during the ablation procedure. In addition, the surgeon may continue to deliver the neurostimulation current following the ablation procedure before withdrawing probe 50 from the target tissue site.

Delivering ablation current and neurostimulation current via separate conductors avoids the need to coordinate delivery along a single conductor, including the need for any circuitry that may be needed to protect neurostimulation current generator 19 from the ablation current. Even with separate conductors, however, protection circuitry, such as diodes, transient spike filters, and the like, may be needed to avoid cross-conduction between needle 52 and electrode 70. Alternatively, neurostimulation current generator 19 may be disabled during delivery of ablation current to avoid damage to the neurostimulation circuitry.

Figure 6:
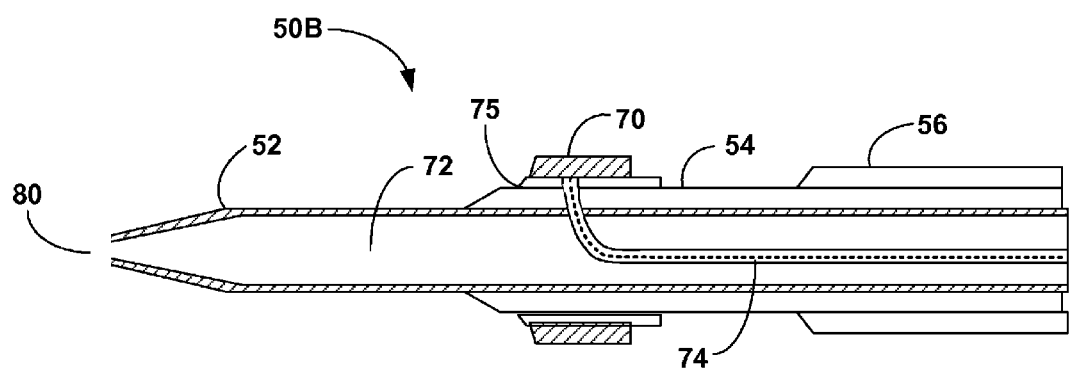
FIG. 6 is an enlarged cross-sectional side view of a biopsy probe with a discrete neurostimulation electrode for the device of FIG. 1.

FIG. 6 is an enlarged cross-sectional side view of a biopsy probe 50C with a discrete neurostimulation electrode 70 for device 10 of FIG. 1. In the example of FIG. 6, biopsy probe 50C need not deliver ablation energy. Rather, needle 52 may be equipped with a port 80 to cut and capture prostate tissue for analysis. In some embodiments, capture and retention may be aided by application of vacuum pressure to lumen 70. In this case, neurostimulation current may be delivered via electrode 70, or needle 52, to prevent or relieve pain caused by penetration of biopsy probe 50C into the prostate tissue. Accordingly, although illustrated for purposes of example, a electrode 70 for delivery of neurostimulation current may be unnecessary. In other embodiments, however, it may be desirable to deliver electrical current via needle 52 at a level sufficient to cauterize tissue surrounding the needle. In other words, upon capture of tissue, the surgeon may apply cauterization current before withdrawing the biopsy probe 50C from the target tissue site.

Figure 7:
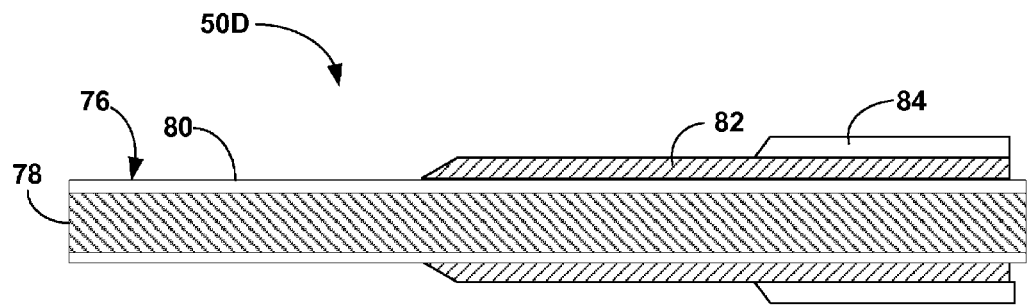
FIG. 7 is an enlarged cross-sectional side view of a laser-based ablation probe with a discrete neurostimulation electrode for the device of FIG. 1

FIG. 7 is an enlarged cross-sectional side view of a laser-based ablation probe 50D with an optical waveguide 76 and discrete neurostimulation electrode 82 for use with device 10 of FIG. 1. Optical waveguide 78 includes an optically transmissive core 78 and an electrically insulative cladding 80. Electrode 82 extends about cladding 80. A dielectric sleeve 84 extends about electrode 82, and exposes a portion of electrode 82 for contact with tissue within the target tissue site. Electrode 82 is coupled to a conductor that runs along the length of catheter 20.

In operation, the surgeon advances probe 50D into the target tissue site, and then delivers neurostimulation current via electrode 82. Then, the surgeon activates ablation energy generator 18, in this case a laser generator, to transmit laser energy for ablation of tissue within the target tissue site via optical waveguide 78. Optical waveguide 78 may emit the laser energy via a distal tip of the waveguide. The laser energy may have a wavelength in the range of approximately 800 to 850 nanometers. Alternatively, optical waveguide 78 may have cladding removed in a selected region to enable lateral emission, i.e., side-firing laser emission.

Neurostimulation current may be applied via electrode 82 before, during and after application of the ablation energy to alleviate pain otherwise experienced by the patient due to the ablation procedure. Again, neurostimulation current may continue to be applied following termination of delivery of the laser energy, but before withdrawal of probe 50D from the target tissue site.

Laser ablation probe 50D depicts an additional type of ablation probe with which neurostimulation may be used. Other examples include microwave antennas or cryogenic probes. In each case, a neurostimulation electrode may be integrated with the probe or provided as a discrete electrode.

Figure 8:
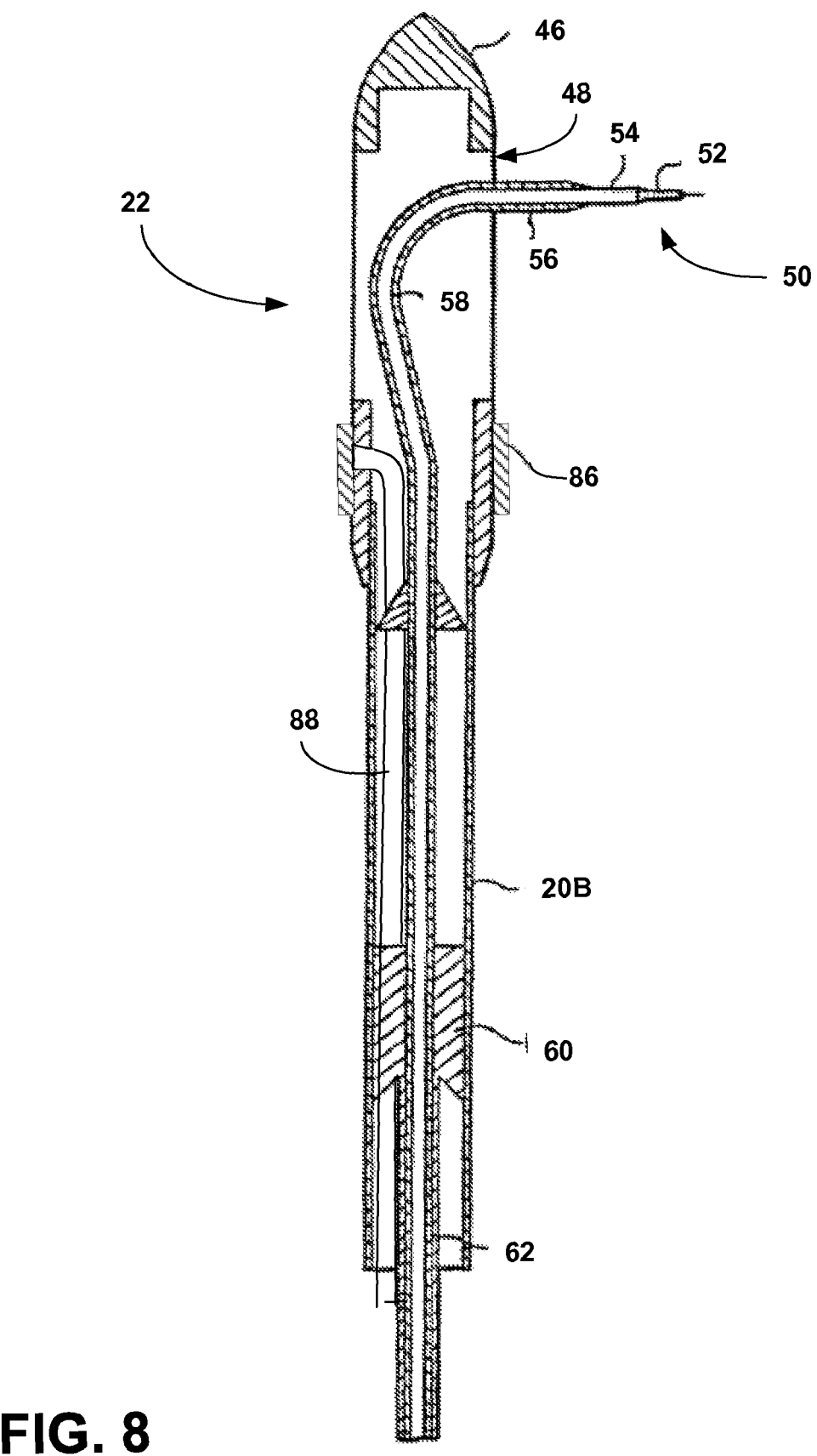
FIG. 8 is an enlarged cross-sectional side view of the distal end of the device of FIG. 1 incorporating a neurostimulation electrode for contact with the urethral wall.

FIG. 8 is an enlarged cross-sectional side view of the distal end 22 of a catheter 20B incorporating a neurostimulation electrode 86 for contact with the urethral wall. Catheter 20B generally conforms to catheter 20A, and may be used to deliver neurostimulation current to the prostate via needle 52. However, catheter 20B further includes an electrode 86 mounted about an exterior of the catheter body for delivery of neurostimulation therapy to the urethral wall, e.g., during introduction of the catheter. Also, neurostimulation therapy can be applied to the urethral wall during withdrawal of catheter 20B from the urethra. Electrode 86 may be a conductive pad or a ring electrode. Electrode 86 may be coupled to neurostimulation current generator 19 via a conductor 88 housed within catheter 20B.

Using catheter 20B, a surgeon can apply neurostimulation therapy to the patient before probe 50 penetrates the target tissue site, and even before distal end 22 reaches the target tissue site. In this manner, neurostimulation therapy can be delivered to the urethral wall to alleviate pain associated with deployment of catheter 20B within the urethra. In addition, once distal end 22 reaches the target tissue site, the neurostimulation therapy can be delivered to the urethral wall proximate the target tissue site to prevent or alleviate pain associated with penetration of the urethral wall and the prostate tissue by probe 50.

Figure 9:
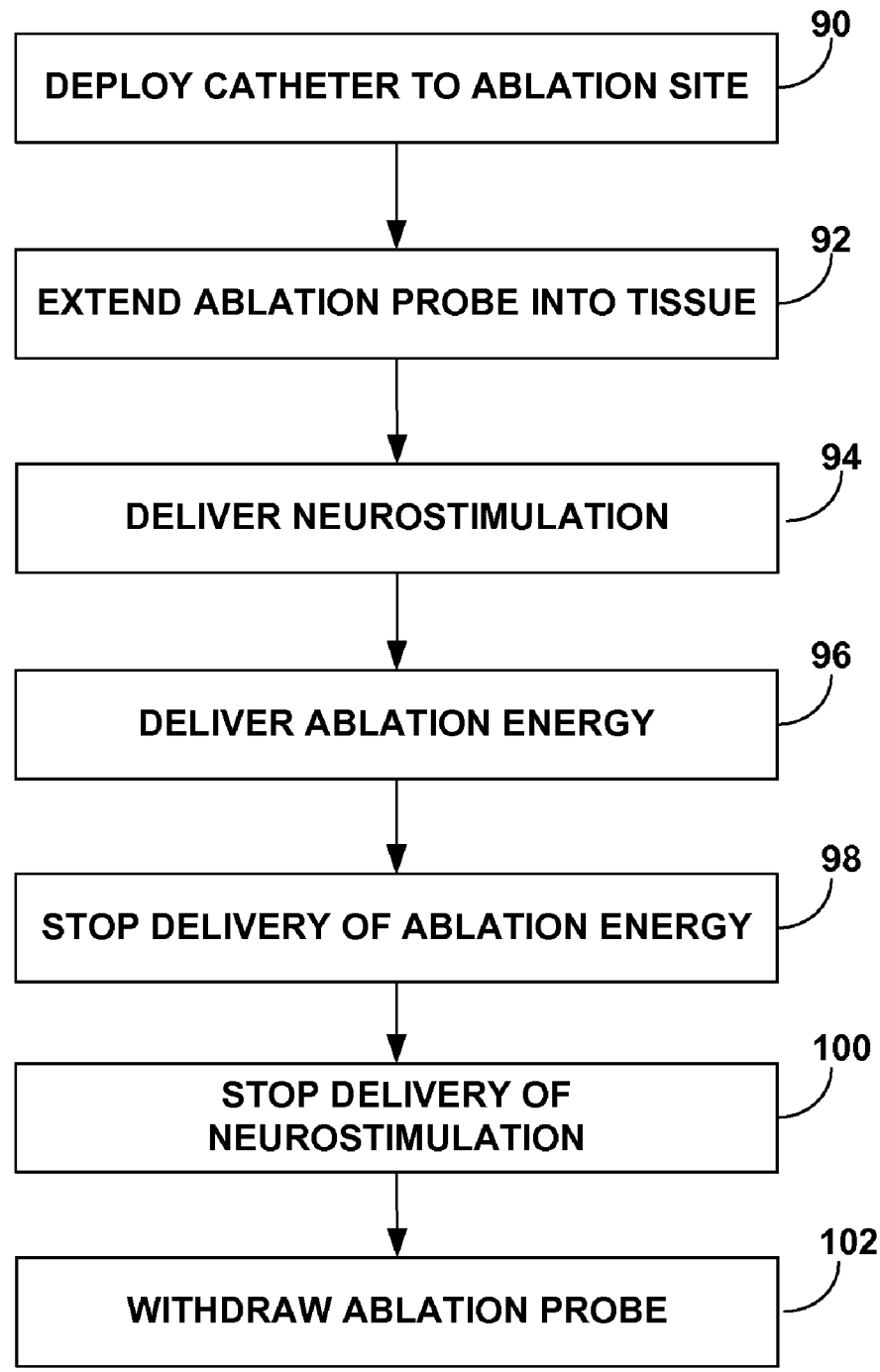
FIG. 9 is a flow diagram illustrating a transurethral ablation procedure.

FIG. 9 is a flow diagram illustrating a transurethral ablation procedure. As shown in FIG. 9, the procedure involves deploying a catheter to an ablation site (90), e.g., the prostate reach by transurethral deployment. Upon extension of the ablation probe into the target tissue (92), neurostimulation current is applied (94) to prevent or alleviate pain associated with the penetration of the urethral wall and prostate tissue, as well as pain associated with delivery of ablation energy. Much of the pain associated with ablation occurs within the first thirty to sixty seconds of creating a lesion. Therefore, pre-treatment of the prostate tissue may be sufficient to provide significant pain relief during that period of time. Ablation energy is delivered via the probe (96) to ablate cells with the target tissue site. When delivery of the ablation energy is stopped (98), neurostimulation delivery may also be stopped (100), or delayed for a period of time following termination of the ablation energy. Then, the ablation probe is withdrawn from the patient (102)

Figure 10:
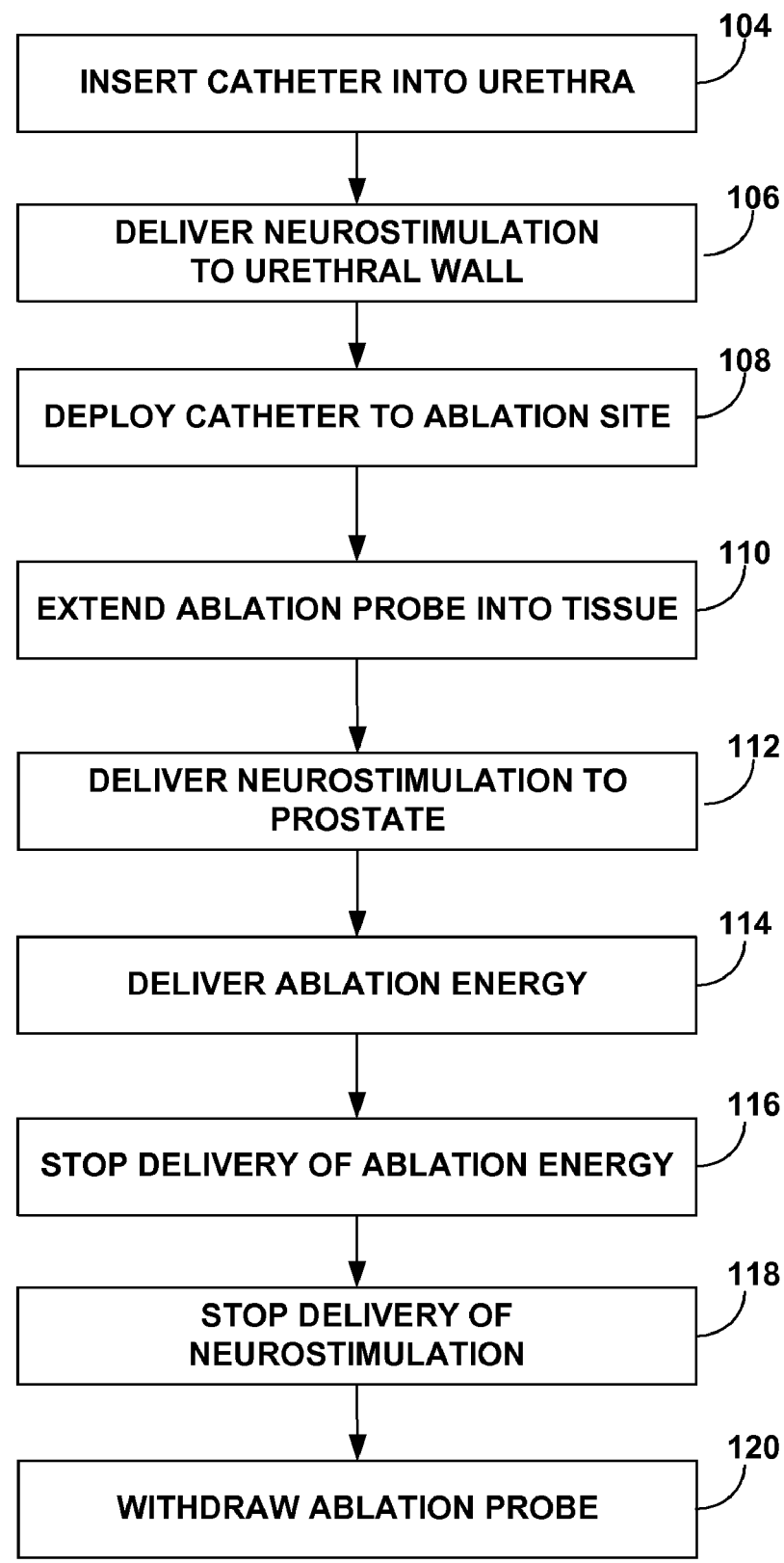
FIG. 10 is a flow diagram illustrating another transurethral ablation procedure.

FIG. 10 is a flow diagram illustrating another transurethral ablation procedure. As shown in FIG. 10, the procedure involves inserting the catheter into the urethra (104), delivering neurostimulation to the urethral wall via an electrode carried by the catheter (106) and deploying a catheter to an ablation site (108), e.g., the prostate reached by transurethral deployment. Upon extension of the ablation probe into the target tissue (110), neurostimulation current is applied (112) via an electrode on or integrated with the ablation probe to prevent or alleviate pain associated with the penetration of the urethral wall and prostate tissue, as well as pain associated with delivery of ablation energy. Ablation energy is then delivered via the probe (114) to ablate cells with the target tissue site. When delivery of the ablation energy is stopped (116), neurostimulation delivery may also be stopped (118), or delayed for a period of time following termination of the ablation energy. Then, the ablation probe is withdrawn from the patient (120).

As further features, a controller may be provided to coordinate the timing and duration of delivery of ablation current and neurostimulation current by ablation current generator 18 and neurostimulation current generator 19, respectively. For example, the controller may execute a surgeon-programmable routine to selectively activate and discontinue neurostimulation during the course of ablation. In addition, in some embodiments, the patient may have the capability to control neurostimulation amplitude settings so as the produce a more acceptable degree of pain relief during the procedure.

Also, rather than integrate neurostimulation capabilities with a transurethral ablation device 10, it is conceivable that neurostimulation can be delivered via a separate neurostimulation probe. For example, a neurostimulation probe may be delivered rectally to a position proximate the prostate tissue. As a further alternative, neurostimulation can be delivered by a transcutaneous neurostimulator.

The preceding specific embodiments are illustrative of the practice of the invention. It is to be understood, therefore, that other expedients known to those skilled in the art or disclosed herein may be employed without departing from the invention or the scope of the claims. For example, the present invention further includes within its scope methods of making and using systems for transurethral ablation, as described herein.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

Many embodiments of the invention have been described. Various modifications may be made without departing from the scope of the claims. These and other embodiments are within the scope of the following claims.

The invention claimed is:

1. A transurethral ablation device comprising:
   a catheter body;
   a neurostimulation energy generator configured to deliver neurostimulation energy to a patient to prevent or relieve pain;
   an ablation energy generator configured to deliver ablation energy to a patient to achieve cell destruction;
   an electrically conductive needle extendable from the catheter body and electrically connected to the ablation energy generator, the electrically conductive needle delivering ablation current received from the ablation energy generator to a prostate of a patient; and
   a neurostimulation electrode extendable from the catheter body and electrically connected to the neurostimulation energy generator, the neurostimulation electrode delivering neurostimulation current received from the neurostimulation energy generator to the patient.

2. The device of claim 1 wherein the neurostimulation electrode is integrated with the needle.

3. The device of claim 1 wherein the neurostimulation electrode includes a ring electrode mounted adjacent the needle.

4. The device of claim 1 further comprising a second neurostimulation electrode mounted on an outer surface of the catheter to deliver neurostimulation energy to a wall of a urethra of the patient.

5. A transurethral ablation device comprising:
   a catheter;
   a neurostimulation energy generator configured to deliver neurostimulation energy to a patient to prevent or relieve pain;
   an ablation energy generator configured to deliver ablation energy to a patient to achieve cell destruction;
   an ablation probe operably extendable from the catheter;
   a neurostimulation probe operably extendable from the catheter;

one or more electrical conductors connected to the ablation energy generator and the neurostimulation energy generator and connected to the ablation probe and the neurostimulation probe to deliver ablation current and neurostimulation current received from the ablation current generator and the neurostimulation current generator, respectively, to the ablation probe and the neurostimulation probe, respectively, the one or more electrical conductors positioned inside the catheter.

6. The transurethral ablation device of claim 5 wherein one electrical conductor is operably connected to the neurostimulation probe and the ablation probe, the electrical conductor delivering both the neurostimulation current and the ablation current to the respective probe.

7. The transurethral ablation device of claim 6 wherein the ablation current and the neurostimulation current are transmitted along the one electrical conductor in a time multiplexed manner or a superimposed manner.

8. The transurethral ablation device of claim 5 further comprising a reference electrode extendable from the catheter.

9. The transurethral ablation device of claim 5 wherein the catheter is coupled to a reference electrode.

10. A transurethral ablation device for treating benign prostate hypertrophy comprising:
   a catheter for insertion into the urethra of a male patient;
   a neurostimulation energy generator configured to deliver neurostimulation energy to a patient to prevent or relieve pain;
   an ablation energy generator configured to deliver ablation energy to a patient to achieve cell destruction;
   an ablation probe operably extendable from the catheter to penetrate a prostate of a patient and electrically connected to the ablation energy generator;
   a neurostimulation probe operably extendable from the catheter and electrically connected to the neurostimulation energy generator;
   one or more electrical conductors connected to the ablation probe and the neurostimulation probe to deliver ablation current and neurostimulation current received from the ablation current generator and the neurostimulation current generator, respectively, to the ablation probe and the neurostimulation probe, the one or more electrical conductors positioned inside the catheter.

11. The device of claim 10 wherein the neurostimulation probe is a neurostimulation electrode.

12. The device of claim 11 wherein the neurostimulation electrode is a needle.

13. The device of claim 12 further including a ring electrode mounted adjacent to the needle.

14. The device of claim 11, further comprising a second neurostimulation electrode mounted on an outer surface of the catheter to deliver neurostimulation energy to a wall of a urethra of the patient.

15. The transurethral ablation device of claim 14 wherein the ablation probe further comprises a needle.

16. The transurethral device catheter of claim 14 wherein the neurostimulation probe further comprises an electrically conductive needle.

17. The transurethral ablation device of claim 16 wherein the neurostimulation probe is moveable within the catheter.

18. The transurethral ablation device of claim 10 wherein the neurostimulation probe is configured to give current in the range of approximately 50 to 150 Hz.

\* \* \* \* \*